US00PP15529P2

(12) United States Plant Patent
Talmadge

(10) Patent No.: US PP15,529 P2
(45) Date of Patent: Feb. 1, 2005

(54) **INTERSPECIFIC *DIASCIA* PLANT NAMED 'BALWINCOR'**

(50) Latin Name: ***Diascia barbarae*×*Diascia integerimma*×*Diascia mollis***
Varietal Denomination: Balwincor

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/734,852
(22) Filed: Dec. 12, 2003
(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Wood, Phillips, Katz, Clark & Mortimer

(57) ABSTRACT

A new and distinct *Diascia* plant named 'Balwincor', characterized by its coral-colored flowers, medium green-colored foliage, and spreading and trailing growth habit.

1 Drawing Sheet

Latin name of genus and species of plant claimed: *Diascia barbarae*×*Diascia integerimma*×*Diascia mollis.*
Variety denomination: 'Balwincor'.

BACKGROUND OF INVENTION

The present invention relates to a new and distinct Interspecific *Diascia* plant hereinafter referred to by the cultivar name 'Balwincor'.

The new cultivar was developed by the inventor in a controlled breeding program during June 2000, at Guadalupe, Calif. The objective of the breeding program was the development of *Diascia* cultivars with a well-branched, spreading growth habit, continuous flowering and medium green foliage.

The female (seed) parent of 'Balwincor' was the proprietary Interspecific *Diascia* selection designated '316-2m-1' (not patented) characterized by its coral-colored flowers, dark green foliage and bushy growth habit. The male (pollen) parent of 'Balwincor' was the proprietary Interspecific *Diascia* selection designated '400-2' (not patented), characterized by its light lavender-colored flowers, dark green foliage and prostrate growth habit. 'Balwincor' was discovered and selected in December, 2000 as a single flowering plant from within the progeny of the above stated cross-pollination and was initially designated '593-3m-2-1-1'.

Asexual reproduction of the new cultivar by terminal stem cuttings since December 2000 at Guadalupe, Calif. and West Chicago, Ill., has demonstrated that the new cultivar reproduces true to type with all the characteristics, as herein described, firmly fixed and retained through successive generations of such asexual propagation.

SUMMARY OF INVENTION

The new cultivar has not been observed under all possible environmental conditions to date. Accordingly, it is possible that the phenotype may vary somewhat with variations in the environment, such as temperature, light intensity, and day length.

It was repeatedly found that the cultivar of the present invention:

1. Exhibits coral-colored flowers,
2. Forms foliage of a medium green color, and
3. Exhibits a spreading and trailing growth habit.

Plants of the new cultivar differ from plants of the female parent primarily in foliage color and from plants of the male parent primarily in flower and foliage color.

The new cultivar can be compared to the commercially available *Diascia* variety Sun Chimes Peach(not patented). However, in side by side comparisons, plants of the new cultivar differ from plants of Sun Chimes Peach in the following characteristics:

1. The flowers of the new cultivar are larger,
2. The flowers of the new cultivar are lighter in color, and
3. The leaves of the new cultivar are larger.

BRIEF DESCRIPTION OF PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balwincor'. The plants were grown for 10 weeks in a greenhouse at West Chicago, Ill.

DETAILED BOTANICAL DESCRIPTION

Figure 1:
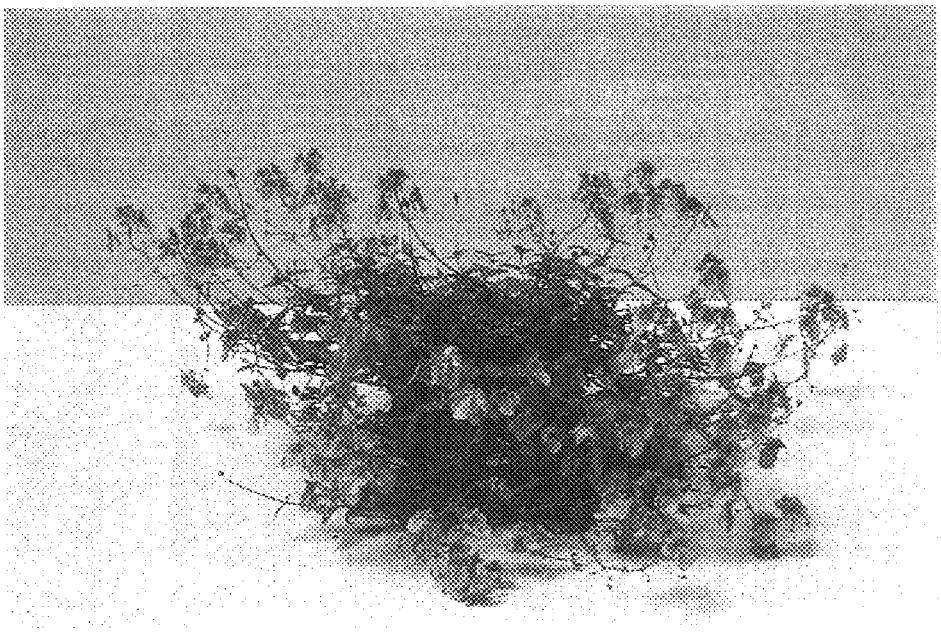
FIG. 1 illustrates a side view of the overall growth and flowering habit of the new cultivar.
Figure 2:
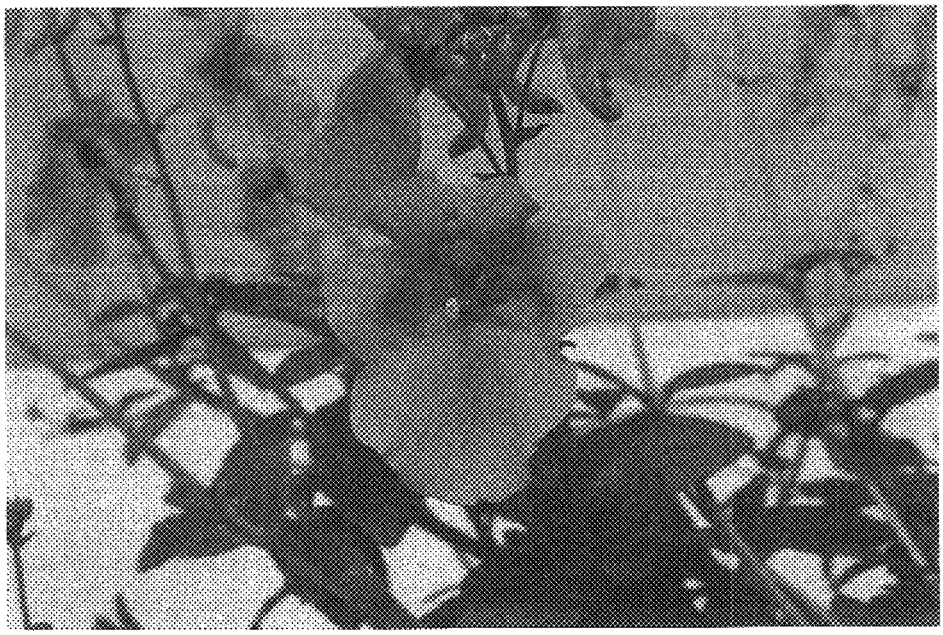
FIG. 2 illustrates a close up view of individual flowers of the new cultivar.

The new cultivar has not been observed under all possible environmental conditions to date. Accordingly, it is possible that the phenotype may vary somewhat with variations in the environment, such as temperature, light intensity, and day length.

The chart used in the identification of colors described herein is the R.H.S. Colour Chart of The Royal Horticultural Society, London, England, 1995 edition except where general color terms of ordinary dictionary significance are used. The color values were determined on Jul. 23, 2003. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown in 10 cm pots for 10 weeks while utilizing a soilless growth medium. Greenhouse temperatures were maintained at approximately 62° to 75° F. (17° to 24° C.) during the day and approximately 52° to 60° F. (11° to 15° C.) during the night. Greenhouse light levels were maintained at approximately 5,000–8,000 footcandles during the day.

Botanical classification: Interspecific *Diascia* cultivar 'Balwincor'.

Parentage:

*Female parent.*—Proprietary Interspecific *Diascia* selection designated '316-2m-1' (not patented).

*Male parent.*—Proprietary Interspecific *Diascia* selection designated '400-2' (not patented).

Propagation:

*Type cutting.*—Terminal stem.

*Time to initiate roots.*—Approximately 14 to 21 days.

*Root description.*—Fibrous, branching.

Plant description:

*Crop time.*—Approximately 5 to 7 weeks from planting of rooted cuttings in a 10 cm pot.

*Habit of growth.*—Vigorous. Forms lateral branches at every node. A mature plant, 10 weeks after the planting of a rooted cutting, measures approximately 19.2 cm in height and approximately 63.4 cm in width with approximately 55 lateral flowering branches.

*Form.*—Spreading, trailing.

*Lateral branch.*—Shape: Square. Length: Approximately 34 cm. Diameter: Approximately 1.6 mm. Texture: Glabrous. Internode length at middle of branch length: 4.4 cm. Color: 144B.

*Foliage.*—Type: Simple. Arrangement: Opposite. Shape: Ovate. Margin: Dentate. Apex: Acute. Base: Cordate. Texture: Glabrous to Puberulent. Quantity of leaves per lateral branch: Approximately 10.8. Leaf length: Approximately 3 cm. Leaf width: Approximately 2.3 cm. Leaf orientation to stem: Obtuse to parallel. Leaf fragrance: None. Venation pattern: Pinnate. Color of mature foliage: Upper surface: 137A with venation of 138B. Color of mature foliage: Lower surface: 137B with venation of 138B. Petiole length: Approximately 6 mm. Petiole diameter: Approximately 1.8 mm. Petiole texture: Upper and lower surfaces: Glabrous. Petiole color: Closest to 144B.

Flowering description:

*Flowering habit.*—Freely flowering.

*Natural flowering season.*—Year round in greenhouse environment and spring through autumn in outdoor garden.

*Flower arrangement.*—Terminal racemes.

*Raceme description.*—Length: 4.1 cm. Width: 3.9 cm. Number of flowers per raceme: Approximately 3.

Flower description:

*Type.*—Solitary, five lobed and zygomorphic with double nectar spurs.

*Fragrance.*—None.

*Aspect.*—Concave.

*Lastingness of individual bloom.*—Approximately 5 days.

*Flower.*—Shape: Oblong. Width: Approximately 1.9 cm. Length: Approximately 2.1 cm. Depth: Approximately 1 cm.

*Petals.*—Number: Five, non-imbricate and fused at base. Shape: Obovate. Margin: Entire. Apex: Obtuse. Aspect: Cupped.

*Two upper (banner) petals.*—Length: Approximately 5 mm. Width: Approximately 6 mm. Texture of upper surface: Glabrous. Texture of lower surface: Moderately glandular. Gland color: 83B. Color of upper surface: 48B with indentation of 7A. Color of lower surface: 48C.

*Lateral petals.*—Length: Approximately 6 mm. Width: Approximately 8 mm. Texture of upper and lower surface: Glabrous. Color of upper surface: 48B. Color of lower surface: 48C. Sharply curved nectar spurs form at base of each of the lateral petals.

*Nectar spurs.*—Length: 8.3 mm. Diameter at base: 2 mm. Diameter at tip: 1 mm. Color: 48D with tip of 187A.

*Lower petal.*—Length: Approximately 1 cm. Width: Approximately 1.3 cm. Texture of upper and lower surface: Glabrous. Color: Upper of surface: 48C. Color of lower surface: 48D.

*Sepals.*—Quantity: 5. Shape: Lanceolate. Length: Approximately 4 mm. Width: Approximately 1 mm. Apex: Acute. Margin: Entire. Texture: Upper surface: Moderately glandular pubescent. Glands: 71A. Lower surface: Glabrous. Color: Upper and lower surfaces: 137A–146A. Calyx shape: Star. Calyx length: Approximately 4 mm. Calyx diameter: Approximately 6 mm.

*Peduncle.*—Length: Approximately 5.1 cm. Diameter: Approximately 1 mm. Aspect: At acute angle to branch. Texture: Moderately pubescent. Color: 143C.

*Bud.*—Shape: Oval, flat. Length: Approximately 8.5 mm. Diameter: Approximately 7.5 mm. Color: 38D.

*Reproductive organs.*—Androecium: Stamen quantity: Four per flower. Filament length: Approximately 3 mm. Filament color: Anther shape: Oval. Anther length: 1 mm. Anther color: 12B. Amount of pollen: Abundant. Pollen color: 13A. Gynoecium: Pistil quantity: One per flower. Pistil length: 4.3 mm. Stigma shape: Round. Stigma length: 0.3 mm. Stigma color: 154C. Style length: Approximately 2 mm. Style color: 150C. Ovary length: Approximately 2 mm. Ovary color: 144B.

Seed and fruit production: Neither seed nor fruit production has not been observed.

Disease and pest resistance: Resistance to pathogens and pests common to *Diascia* has not been observed.

Hardiness zone: 'Balwincor' is hardy in zones nine (9) and above.

What is claimed is:

1. A new and distinct cultivar of Interspecific *Diascia* plant named 'Balwincor' substantially, as herein shown and described, which:

1. Exhibits coral-colored flowers,
2. Forms medium green-colored foliage, and
3. Exhibits a spreading and trailing growth habit.

* * * * *